(12) United States Patent
Crainich

(10) Patent No.: US 7,867,243 B2
(45) Date of Patent: Jan. 11, 2011

(54) TISSUE GRASPING AND CLIPPING/STAPLING DEVICE

(75) Inventor: Lawrence Crainich, Charlestown, NH (US)

(73) Assignee: Design Standards Corporation, Charlestown, NH (US)

( * ) Notice: Subject to any disclaimer, the term of this patent is extended or adjusted under 35 U.S.C. 154(b) by 928 days.

(21) Appl. No.: 09/948,341

(22) Filed: Sep. 6, 2001

(65) Prior Publication Data

US 2003/0045890 A1    Mar. 6, 2003

(51) Int. Cl.
*A61B 17/10* (2006.01)
(52) U.S. Cl. ..................................... 606/142
(58) Field of Classification Search ................. 606/138, 606/139, 142–143, 205, 206, 207, 208
See application file for complete search history.

(56) References Cited

U.S. PATENT DOCUMENTS

| | | | | | |
|---|---|---|---|---|---|
| 2,277,139 | A | * | 3/1942 | Niemand | 72/409.05 |
| 4,166,466 | A | * | 9/1979 | Jarvik | 606/143 |
| 4,706,668 | A | * | 11/1987 | Backer | 606/142 |
| 5,518,164 | A | * | 5/1996 | Hooven | 227/5 |
| 5,601,573 | A | * | 2/1997 | Fogelberg et al. | 606/143 |
| 5,601,578 | A | * | 2/1997 | Murphy | 606/148 |
| 5,833,695 | A | * | 11/1998 | Yoon | 606/139 |
| 5,906,625 | A | * | 5/1999 | Bito et al. | 606/142 |
| 5,954,731 | A | * | 9/1999 | Yoon | 606/144 |
| 5,984,939 | A | * | 11/1999 | Yoon | 606/170 |
| 6,139,563 | A | * | 10/2000 | Cosgrove et al. | 606/205 |
| 6,494,888 | B1 | * | 12/2002 | Laufer et al. | 606/153 |

* cited by examiner

*Primary Examiner*—Michael J Milano
*Assistant Examiner*—Victor X Nguyen
(74) *Attorney, Agent, or Firm*—Bachman & LaPointe, P.C.

(57) ABSTRACT

A tissue grasping and clipping/stapling device includes a grasping jaw assembly for grasping tissue, and a fastener delivery and forming assembly adapted for applying a fastener to tissue grasped with the jaw assembly. The jaw assembly has a spring loaded closing mechanism to secure different thicknesses of tissue and the fastener feeding and applying mechanism is adaptable to different extents of closing of the jaw assembly. The device is particularly well suited for miniature clipping/stapling such as anastomosis of coronary blood vessels and the like.

26 Claims, 4 Drawing Sheets

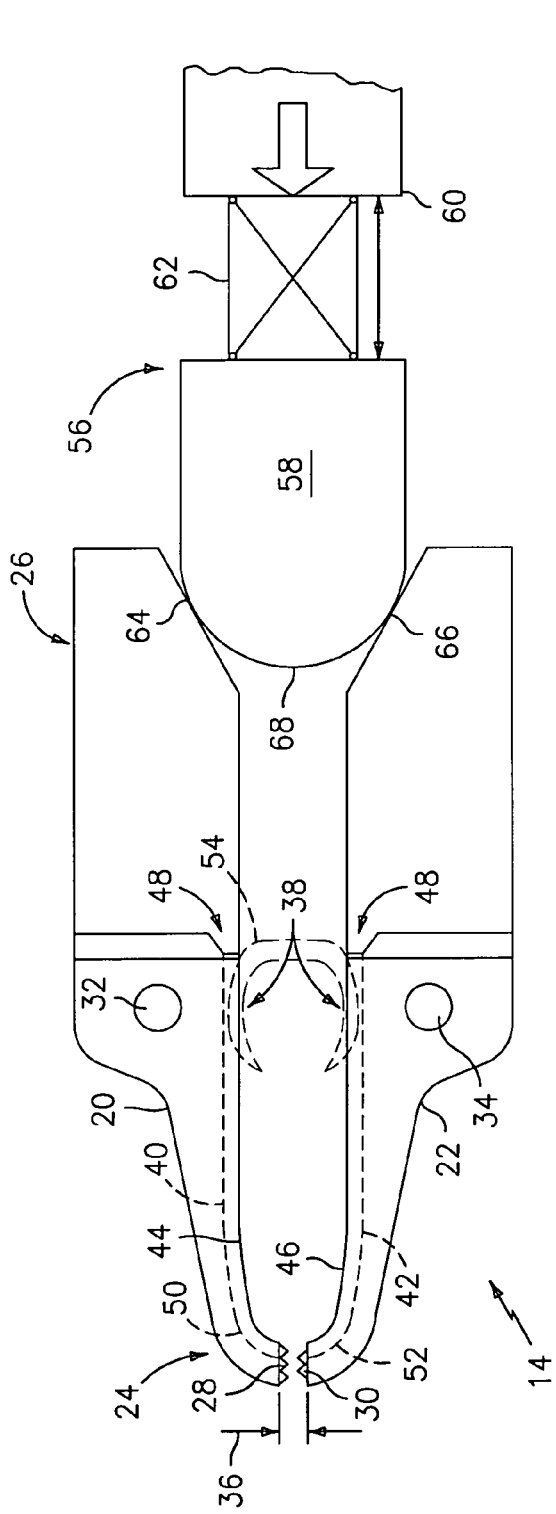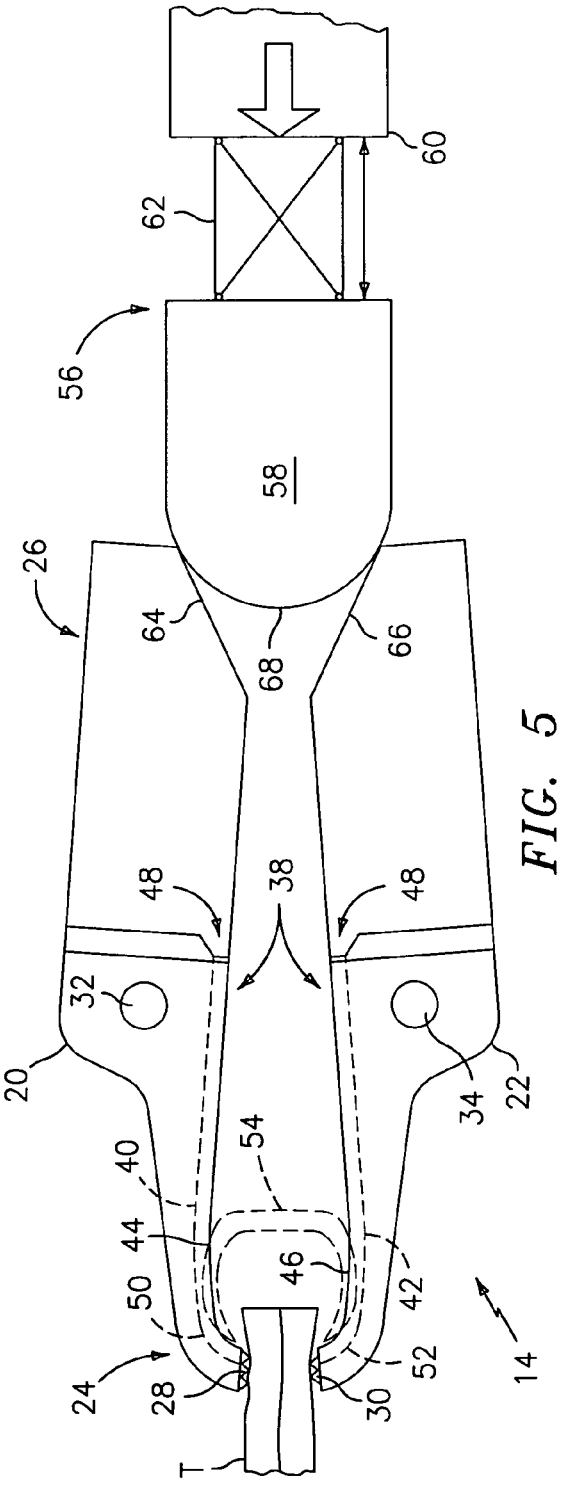
FIG. 4
FIG. 5

TISSUE GRASPING AND CLIPPING/STAPLING DEVICE

BACKGROUND OF THE INVENTION

The invention relates to a tissue grasping and clipping/stapling device which is useful for grasping and fastening tissue utilizing a single implement, and without the need for sutures and the like. A particular aspect of the invention relates to the forming of a staple and, particularly, the mechanism whereby the staple is formed which is useful with very small staples.

In the course of conducting surgical procedures, various tissues must frequently be secured together, using sutures, surgical staples, clips and the like. In order to obtain a secure fastening of the tissue in question, multiple steps must frequently be used. First, the tissue portions in question must be secured, and these tissues are then conventionally fastened together using a suturing step.

These problems, and others, are exacerbated when the fastener in question is very small.

This can result in a cumbersome procedure, utilizing several different pieces of equipment, and can also require several different steps before clips or staples or other fasteners are eventually secured to the tissue in question.

It is clear that the need remains for improved devices for conducting such clipping or stapling, whereby small fasteners are securely and reliably applied, and wherein the initial separate tissue securing step can be eliminated so as to shorten the duration of surgical procedures and improve the end results of same.

It is therefore the primary object of the present invention to provide an apparatus which greatly simplifies the clipping or stapling of tissue in an effective and secure manner.

It is a further object of the present invention to provide such an apparatus which is simple and reliable in use.

Other objects and advantages of the present invention will appear hereinbelow.

SUMMARY OF THE INVENTION

In accordance with the present invention, the foregoing objects and advantages have been readily attained.

According to the invention, a tissue grasping and clipping/stapling device is provided, which device comprises a grasping jaw assembly for grasping tissue; and a fastener delivery and forming assembly adapted for applying a fastener to tissue grasped with said jaw assembly.

In further accordance with the invention, the grasping jaw assembly is pivotable to various different openings or widths so as to be adaptable to different thicknesses of tissue, and a jaw closing member is spring loaded so as to allow closing of the jaws to stop at the appropriate position depending upon thickness of tissue being grasped.

In accordance with this aspect of the present invention, the jaw assembly therefore defines a spacing between the jaws which is variable depending upon thickness of tissue secured therebetween, and the present invention further provides for a fastener feed assembly which can accommodate these differences in spacing.

In accordance with a still further aspect of the present invention, a tissue grasping and clipping/stapling device is provided, which device comprises a housing; two spaced jaw members extending from said housing and having distal ends, said distal ends being turned inwardly toward each other and having tissue grasping surfaces defined on said ends and facing each other; and a fastener feed and forming track formed on said jaw members for conveying a fastener from said housing to said distal ends.

BRIEF DESCRIPTION OF THE DRAWINGS

A detailed description of preferred embodiments of the present invention follows, with reference to the attached drawings, wherein:

FIGS. 4-6 schematically illustrate an apparatus in accordance with the present invention at positions for grasping different thicknesses of tissue;

DETAILED DESCRIPTION

The invention relates to a tissue grasping and clipping/stapling device which allows for grasping of tissue and applying a fastener such as a surgical staple or clip to the tissue using a single device and in particular, extremely small clips can be applied with this device, for example as used in anastomosis of coronary blood vessels and the like.

Figure 1:
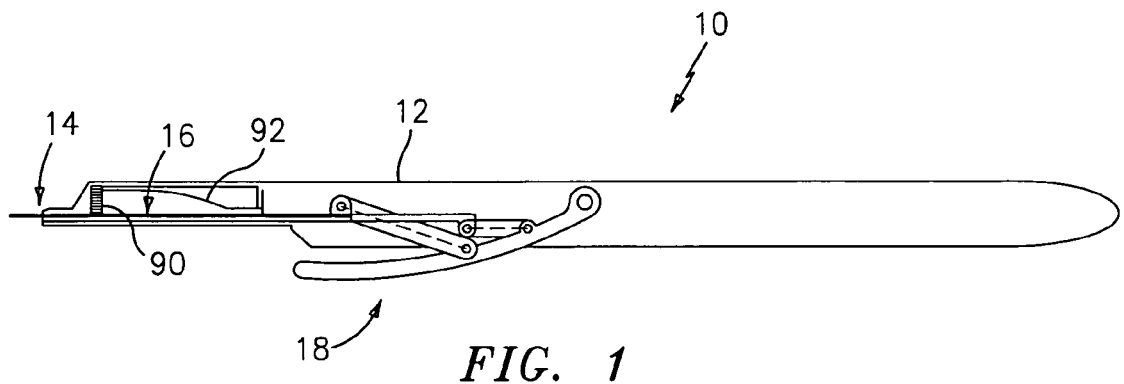
FIG. 1 is a side schematic view of a device in accordance with the present invention.
Figure 2:
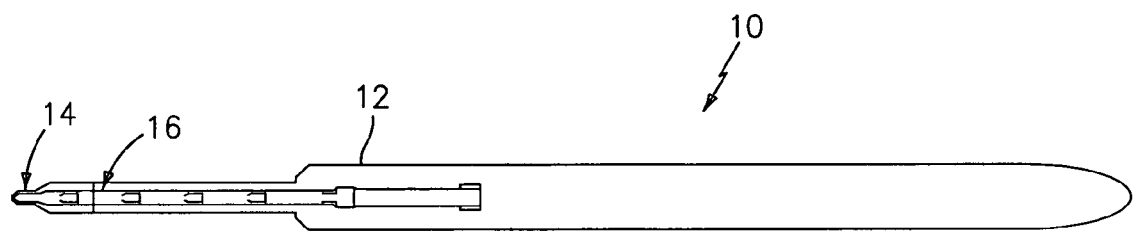
FIG. 2 is a top schematic view of a device in accordance with the present invention.

FIGS. 1 and 2 schematically show an apparatus 10 in accordance with the invention having a housing 12, a grasping jaw assembly 14, and a fastener delivery and forming assembly 16 which is illustrated in greater detail in subsequent figures. FIGS. 1 and 2 also show a trigger assembly 18 which is adapted to actuate jaw assembly 14 to grasp tissue and to actuate fastener delivery and forming assembly 16 so as to position a fastener on tissue grasped by jaw assembly 14.

It should be noted that various portions of the device of the present invention will be referred to herein as distal or proximal. These terms are used based upon the orientation of a user of the device, with distal meaning relatively toward the jaws of the device and proximal meaning relatively toward the handle or user of the device.

Figure 3:
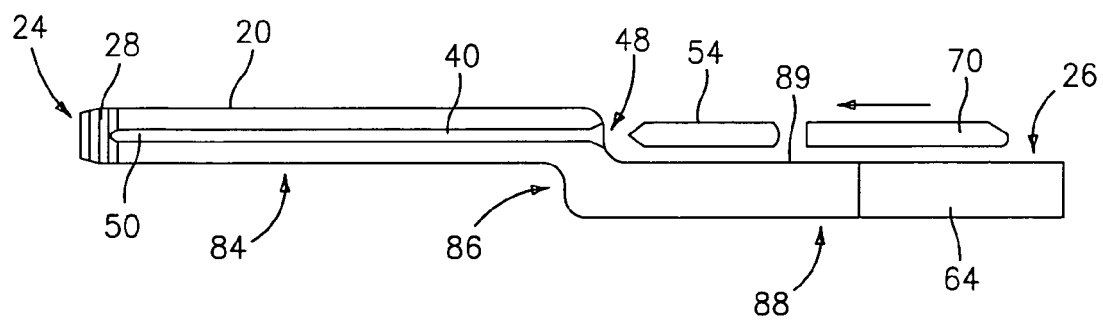
FIG. 3 is an inside view of a jaw member in accordance with the present invention.

FIGS. 3 and 4 better illustrate jaw assembly 14 in accordance with the present invention.

FIG. 4 shows jaw assembly 14 having jaw members 20, 22 which have distal ends 24 and proximal ends 26. As shown, distal ends 24 define thereon tissue grasping surfaces 28, 30, which are disposed on jaw members 20, 22 such that the face each other. Grasping surfaces 28, 30 may suitably have serrations for better gripping as shown in FIGS. 3-5.

Jaw members 20, 22 are preferably movably mounted relative to each other, for example by pivotably mounting to housing 12 at pivot points 32, 34, such that the jaws can be pivoted to an open position wherein a gap 36 defined between tissue grasping surfaces 28, 30 is large enough to receive tissue therebetween. From the open position, jaw members 20, 22 can be pivoted toward a closed position such that tissue grasping surfaces 28, 30 securely grasp tissue in gap 36. Of course, jaw members 20, 22 can be movably mounted relative to each other in different manners, well within the scope of the present invention.

Fastener delivery and forming assembly 16 advantageously includes a fastener delivery and forming track 38 which is defined along jaw members 20, 22 as shown so as to deliver a fastener 54 from a proximal position toward tissue grasping surfaces 28, 30.

As shown, track 38 is preferably defined as track elements 40, 42 formed on inner surfaces 44, 46 of jaw members 20, 22, and facing each other, so as to receive a fastener in sliding fashion.

As shown in FIG. 4, track elements 40, 42 preferably include a straight or conveying portion which extends from a track inlet 48 for a substantially straight distance along jaw members 20, 22. Track 38 preferably further includes fastener forming sections 50, 52 which extend from the straight portions and curve substantially inwardly toward each other as shown in the drawings. When a fastener is pushed into fastener forming sections 50, 52, the fastener is advantageously formed and secured to tissue held by tissue grasping surfaces 28, 30 in gap 36 as desired in accordance with the present invention.

FIG. 3 shows a side view of a jaw member 20 and further illustrates track element 40 and tissue grasping surface 28, along with a fastener 54 in position for conveying along track 38 as desired.

Fastener delivery and forming assembly 16 in accordance with the invention advantageously allows for the secure and rapid application of very small fasteners.

Jaw members 20, 22 are actuated or moved between open and closed positions by a jaw actuating assembly 56 which includes a push member 58, an element 60 to which translation is provided by trigger assembly 18, and a compressible member or buffer member 62 such as a spring or the like which is disposed along jaw actuating assembly 56, for example between element 60 and push member 58, for absorbing additional movement of element 60 once push member 58 has reached a point where the gap between jaw members is appropriate for the tissue grasped therein.

Also as shown, jaw members 20, 22 advantageously have push member contact surfaces 64, 66 which are disposed to interact with push member 58 such that longitudinal translation of push member 58 relative to jaw members 20, 22 pivots jaw members 20, 22 around pivot points 32, 34 between open and closed positions.

In the embodiment shown in FIG. 4, push member 58 advantageously has a substantially rounded front surface 68 which is disposed to smoothly and slidingly interact with contact surfaces 64, 66. Also in this embodiment, contact surfaces 64, 66 are advantageously provided as angled surfaces on proximal ends 26 of jaw members 20, 22, which advantageously slope away from each other in a proximal direction as shown.

As set forth above, it is a particular advantage of the present invention that jaw members 20, 22 can be closed securely about tissues having different thicknesses. This function is provided by compressible member 62 which advantageously serves to absorb a substantial portion of further movement conveyed by trigger assembly 18 after jaw members 20, 22 have closed securely about tissue grasped therebetween, thereby automatically adjusting the gap in the grasping position to the appropriate size for the tissue grasped.

This is particularly advantageous in that tissue to be grasped and fastened in accordance with the present invention is frequently of different thickness from procedure to procedure, and compressible member 62 advantageously allows for apparatus 10 to be used to grasp and secure all different types or thicknesses of tissue without damaging the tissue. The spring loaded closing assembly helps to avoid over-tightly gripping of the tissue. Further, the structure of push member 58 advantageously serves to resist movement of the jaw members 20, 22 due to pressure created by forming a fastener.

The movable mounting of jaw members 20, 22 results in variable track spacing between track elements 40, 42. This spacing is variable between a maximum spacing when jaw members 20, 22 are fully open, and smaller spacings as jaw members 20, 22 are closed to secure tissue. As set forth below, fasteners and the fastener feed assembly are advantageously adapted to function with the maximum spacing and also at the smaller spacings, and are further advantageously provided of resilient material having a rest position which biases toward the maximum spacing.

As shown in FIG. 5, when a tissue T is to be grasped that is substantially thick or heavy, then jaw members 20, 22 will close to a lesser extent, and gap 36 will be larger, while compressible member 62 will absorb a greater amount of the sliding motion conveyed by trigger assembly 18 to element 60 as desired. This advantageously provides for secure grasping of tissue T between tissue grasping surfaces 28, 30, without injuring or damaging such tissue.

Figure 6:
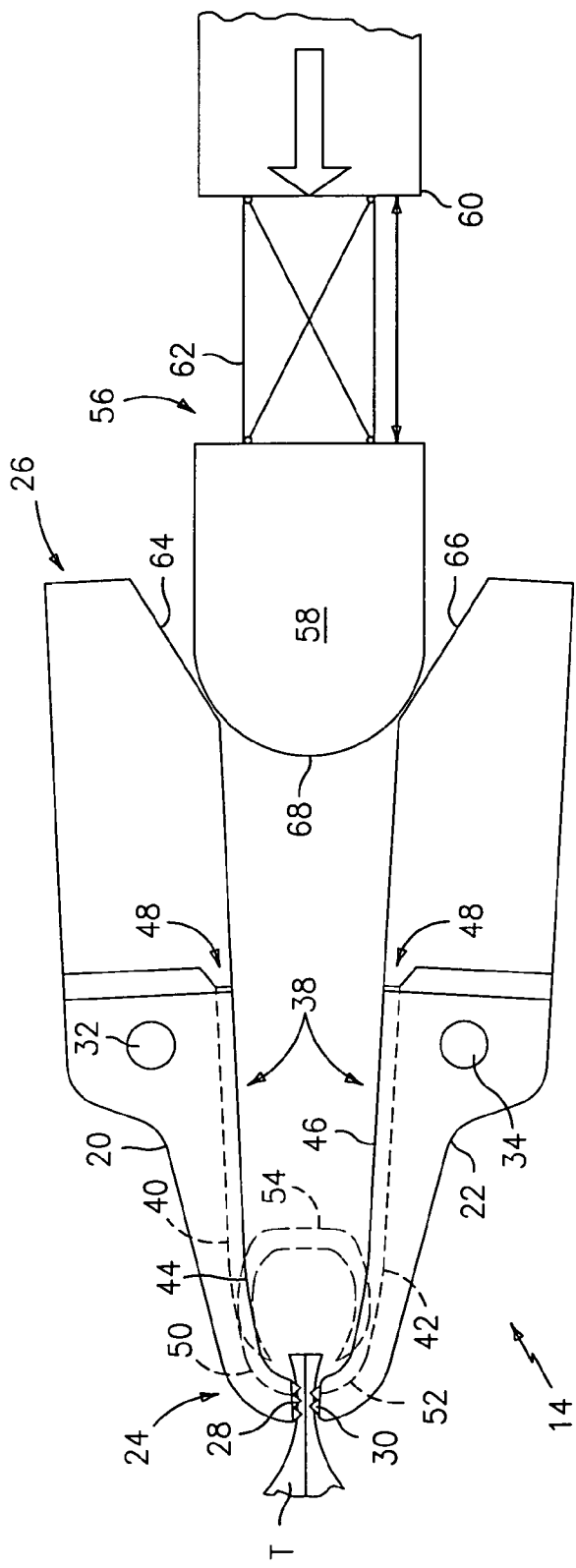

As shown in FIG. 6, when tissue T is thinner, jaw members 20, 22 close to a greater extent, resulting in a smaller gap 36, and further resulting in less or no compression of compressible member 62. This also advantageously results in secure grasping of tissue T without damage or injury to same.

It should be appreciated that proximal or rearward motion of push member 58 advantageously allows jaw members 20, 22 to pivot back toward an open position, and jaw members 20, 22 may be biased toward an open position in accordance with the present invention using any conventional biasing member (not shown).

Figure 7:
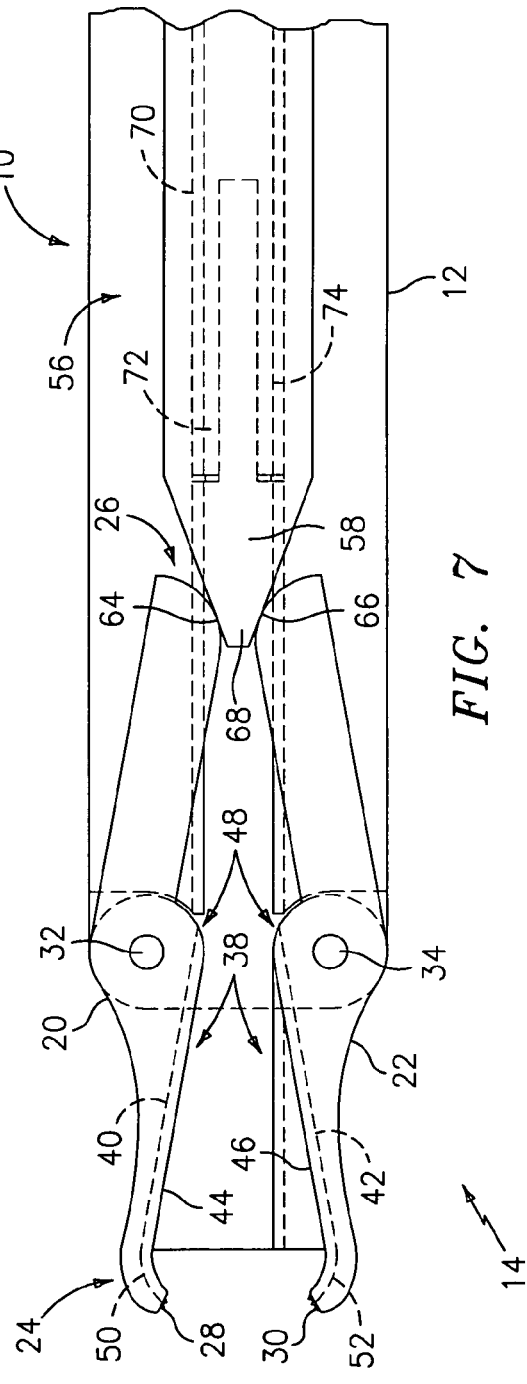
FIG. 7 further schematically illustrates the operation of an apparatus in accordance with the present invention.

FIG. 7 shows apparatus 10 in accordance with the present invention with jaws 20, 22 in an open position for application to or grasping of tissue, with push member 58 in a proximal position.

Figure 8:
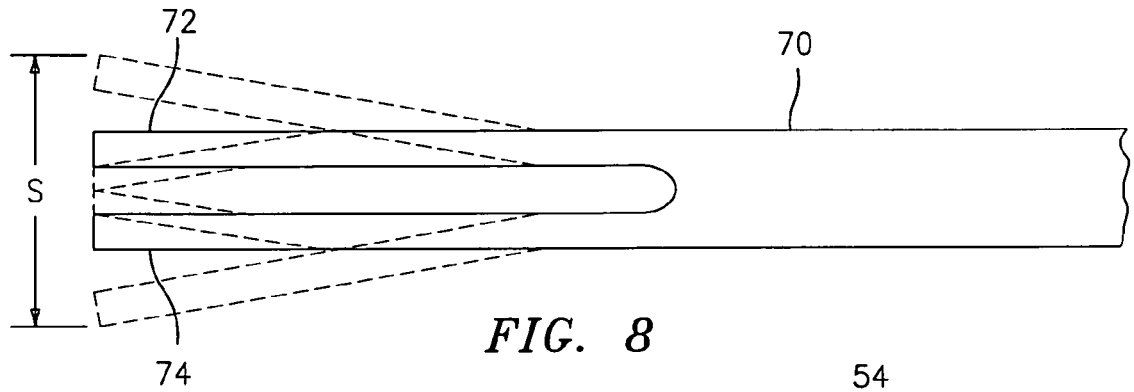
FIG. 8 illustrates a compliant fastener feeding member that forms the clip in accordance with the present invention.

FIG. 8 further illustrates another component of the fastener delivery and forming assembly in the form of a fastener feed or pushing member 70 which is advantageously provided as a slidable pusher member slidably positioned relative to housing 12 and jaw members 20, 22 and having extending prongs 72, 74 which extend distally for contacting a fastener and conveying the fastener along track 38 as desired.

As shown in FIG. 8, prongs 72, 74 are advantageously laterally resilient, and are preferably provided having a rest position wherein prongs 72, 74 are spread laterally as shown in the outer dashed lines in FIG. 8. Prongs 72, 74 are advantageously flexible such that they can be inwardly flexed or compressed to the parallel position shown in solid lines in FIG. 8, and further to the touching or nearly touching position shown by the inner dashed lines in FIG. 8.

This advantageously allows for fastener pushing member 70 to adapt to whatever positioning or spacing S jaw members 20, 22 are at such that a fastener can be conveyed to tissue grasped by tissue grasping surfaces 28, 30, regardless of the thickness of the tissue.

Thus, fastener pushing member 70 advantageously is provided having a compressible width 76 which is biased toward a wide width corresponding to a maximum open position of jaw members 20, 22, and which is readily compressible to a narrower width to correspond to narrower widths between jaw members 20, 22.

Fastener pushing member 70 is advantageously slidably mounted in housing 12 relative to housing 12 and jaw members 20, 22, and is aligned so as to slide over proximal end 26 of jaw members 20, 22 so as to push a clip from a waiting position into track 38 as desired.

Fastener pushing member 70 is advantageously actuated by trigger assembly 18, for example through a sliding member disposed through housing 12.

Figure 9:
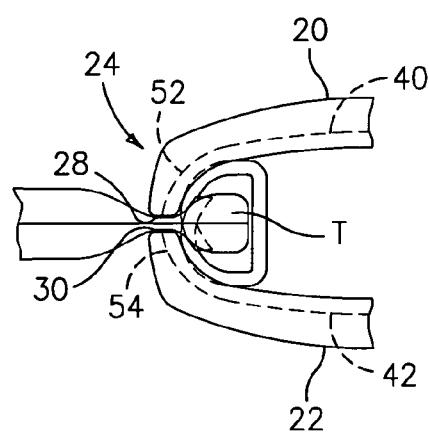
FIG. 9 shows jaws in accordance with the present invention grasping tissue and a staple being fastened thereto.

Turning now to FIG. 9, operation of apparatus 10 in accordance with the present invention is further illustrated, and jaw members 20, 22 are shown grasping tissue T between tissue grasping surfaces 28, 30 such that a fastener 54 conveyed through track 38 will be guided by fastener forming sections 50, 52 of track 38 to securely apply to tissue T as desired. A fastener 54 is shown secured to the tissue as desired.

Figure 10:
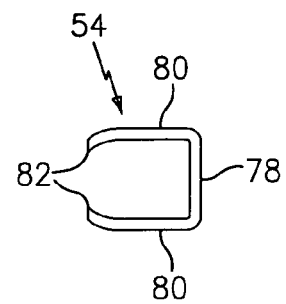
FIGS. 10 and 11 respectively show a staple for use in accordance with the present invention in an open and a closed position.

FIG. 10 illustrates one embodiment of a fastener 54 in accordance with the present invention, in the form of a staple member having a bale section 78, two arms 80 extending substantially parallel to each other from bale 78, and terminal or distal ends 82 which are preferably sharp so as to pierce tissue to be stapled therewith. Ends 82 may be slightly angled inwardly as shown in FIG. 10 so as to smoothly traverse track 38, especially fastener forming sections 50, 52, as desired.

Figure 11:
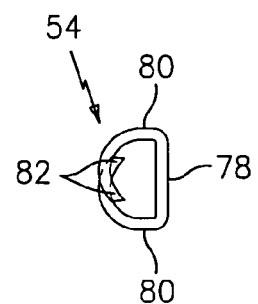

FIG. 11 shows such a fastener 54 in a closed position, after having been closed by track 38, and shows ends 32 substantially overlapping, and arms 80 deformed substantially inwardly, to a position wherein tissue is grasped securely therein.

Figure 12:
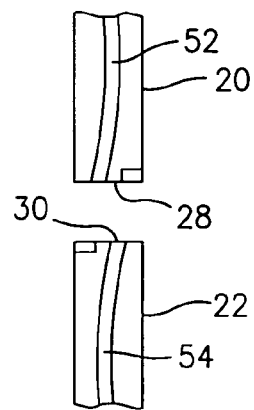
FIG. 12 shows a preferred embodiment of structure for the tips of jaw members in accordance with the present invention which structure is formed so that clip tips will bypass during a forming step.

FIG. 12 shows a preferred embodiment of the present invention wherein a portion of track 38, particularly fastener forming sections 50, 52 are offset in jaw members 20, 22 such that ends 82 of fastener 54 are guided to overlap rather than touch each other directly when fastener 54 is being formed. This further helps in providing a fastener 54 in a closed position as shown in FIG. 11.

Returning to FIG. 3, it is a further advantageous feature of the present invention that jaw members 20, 22 are provided having the distal jaw portion 84 which contains track elements 40, 42 defined in one plane with a stepped portion 86 positioned intermediately, and with proximal portion 88 defined at a different plane from distal jaw portion such that fastener pushing member 70 can readily align with a fastener 54 and convey same along track 38. During positioning of a fastener 54, prongs 72, 74 advantageously follow fastener 54 into track 38 and push fastener 54 against fastener forming sections 50, 52 to close and form fastener 54 around tissue T grasped therein, all as desired. Thus, proximal portion 88 advantageously defines an upper surface 89 that is positioned to seat a clip 54 in proper position for sliding into track 38 as desired.

The resilient nature of fastener pushing member 70, combined with the spring loaded nature of the jaw closing structure, advantageously provide for an apparatus 10 which can be used to grasp and secure tissue of different thickness in rapid succession and without requiring any adjustments to the apparatus.

It should readily be appreciated that apparatus 10 could be used in accordance with the present invention with fasteners of a wide variety. It is most useful, however, with fasteners that are arranged in apparatus 10 for conveyance along track 38 with arms extending in a distal direction. FIGS. 10 and 11 illustrate one such staple, but other types of clips or staples, referred to collectively herein as fasteners, could also be used in accordance with the present invention.

Returning to FIG. 1, such fasteners can be positioned in housing 12, if desired, in a stack 90 which may be biased downwardly by a leaf spring 92 such that fastener pushing member 70 can interact with a bottom-most fastener in stack 90 and push this fastener into and along track 38 as desired. Upon rearward or proximal movement of pushing member 70, the next bottom-most fastener drops into position for application on the next distal movement of pushing member 70. Of course, other storage mechanisms for fasteners could be used in accordance with the present invention.

It should also be appreciated that although FIGS. 1 and 2 show housing 12 defining a hand-held member having a substantially elongate structure and a lever-type trigger member, other configurations for this portion of the device could be used well within the scope of the present invention.

It should be readily appreciated that apparatus 10 provides for the desired function utilizing a single device, and completely eliminates the need for separate suturing steps and/or the cumbersome use of graspers to grasp tissue and separate devices or procedures for accomplishing the securing of this tissue.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. A tissue grasping and clipping/stapling device, comprising:
    a grasping jaw assembly for grasping tissue; and
    a fastener delivery and forming assembly adapted for delivering and applying a fastener to tissue grasped with said jaw assembly, wherein said fastener delivery and forming assembly comprises a fastener conveying track which comprises two substantially continuous spaced tracks, each having a feed portion and a forming portion, wherein each feed portion extends from a housing of the device to the forming portion, and wherein each forming portion extends distally from the feed portion and curves toward the other forming portion .

2. The apparatus according to claim 1, wherein said jaw assembly comprises a first jaw member having a first tissue grasping surface, and a second jaw member having a second tissue grasping surface, said first and second tissue grasping surfaces defining a gap therebetween, and said first and second jaw members being movably mounted relative to each other such that said gap is adjustable.

3. The apparatus according to claim 2, wherein the fastener conveying track is disposed along said first and second jaw members for conveying a fastener toward said first and second tissue grasping surfaces.

4. The apparatus according to claim 3, wherein each of said first and second jaw members comprise first and second elongate members having first and second distal ends, said first and second grasping surfaces being disposed on said first and second distal ends so as to face each other, and wherein said tracks are disposed along said first and second elongate members.

5. The apparatus according to claim 4, wherein said tracks are spaced from each other at a track spacing, and movement of said first and second jaw members relative to each other changes said track spacing.

6. The apparatus according to claim 5, wherein said first and second jaw members are movable relative to each other so as to define a maximum track spacing, and further comprising a fastener disposed in said fastener conveying track and having a rest width sufficient to engage both of said tracks at said maximum track spacing.

7. The apparatus according to claim 6, further comprising a fastener pusher slidably disposed relative to said first and second jaw members for pushing said fastener along said fastener conveying track toward said first and second tissue grasping surfaces.

8. The apparatus according to claim 7, wherein said fastener pusher is positionable between a wide width corresponding to said track at said maximum track spacing, and a narrow width which is smaller than said wide width.

9. The apparatus according to claim 8, wherein said fastener pusher is biased toward said wide width.

10. The apparatus according to claim 8, wherein said fastener pusher has two spaced distally extending members which are flexibly mounted relative to each other so as to be movable between said wide width and said narrow width.

11. The apparatus according to claim 10, wherein said fastener pusher further comprises a slidable pusher member, said distally extending members extending from said slidable pusher member, and said slidable pusher member being slidable relative to said first and second jaw members between a proximal position wherein a fastener can be positioned in said track distally of said distally extending members, and a distal position wherein said fastener is pushed toward said first and second tissue grasping surfaces.

12. The apparatus according to claim 3, wherein said fastener comprises a deformable member having a bale portion, and two arms extending from said bale portion and terminating in two ends, said fastener being positioned in said fastener conveying track with said arms extending distally to said two ends.

13. The apparatus according to claim 12, wherein said spaced tracks comprise two spaced surfaces defined on and running substantially longitudinally along surfaces of said first and second jaw members to define said feed portions, and fastener forming surfaces extending inwardly toward each other from distal ends of said spaced surfaces to define said forming portions, whereby, when said fastener is moved distally along said track, at least one of said arms and said ends engage said fastener forming surfaces so as to close said fastener onto tissue held in said gap.

14. The apparatus according to claim 2, further comprising a push member for closing said first and second jaw members so as to grasp tissue in said gap between said first and second tissue grasping surfaces.

15. The apparatus according to claim 14, wherein said push member is movable between a closing position wherein said first and second jaw members are closed and an open position wherein said first and second jaw members are open, and further comprising an actuator member for moving said push member and a compressible member positioned between said push member and said actuator member wherein, when said first and second jaw members have grasped tissue in said gap, further movement of said actuator member compresses said compressible member so as to allow said first and second jaw members to close to a gap width appropriate to an amount of tissue grasped in said gap.

16. The apparatus according to claim 14, wherein said first and second jaw members are pivotably mounted relative to each other, wherein said first and second jaw members have push member contact surfaces, and wherein movement of said push member in a closing direction contacts said push member with said push member contact surfaces so as to pivot said first and second jaw members toward a closed position.

17. The apparatus according to claim 16, wherein said first and second jaw members have proximal ends and said contact surfaces are positioned on said proximal ends.

18. The apparatus according to claim 17, wherein said contact surfaces slope away from each other in a proximal direction whereby distal movement of said push member relative to said contact surfaces spreads said contact surfaces.

19. The apparatus according to claim 2, further comprising a jaw actuating assembly comprising a push member for closing said jaws around tissue and a buffer member for absorbing additional closing motion of said push member once said tissue is grasped in said gap, whereby said gap is automatically adjusted to said tissue.

20. The apparatus according to claim 1, further comprising a housing, said grasping jaw assembly being mounted to said housing, and said fastener delivery and forming assembly being defined by at least one of said grasping jaw assembly and said housing.

21. A tissue grasping and clipping/stapling device, comprising:
a housing;
two spaced jaw members extending from said housing and having distal ends, said distal ends being turned inwardly toward each other and having tissue grasping surfaces defined on said ends and facing each other; and
a fastener feed and forming track formed on said jaw members for conveying a fastener from said housing to said distal ends, wherein said fastener feed and forming track comprises a fastener conveying track which comprises two substantially continuous spaced tracks, each having a feed portion and a forming portion, wherein each feed portion extends from a housing of the device to the forming portion, and wherein each forming portion extends distally from the feed portion and curves toward the other forming portion.

22. The apparatus according to claim 21, wherein said jaw members are movably mounted to said housing.

23. The apparatus according to claim 22, further comprising a jaw closing assembly disposed in said housing for closing said jaws so as to grasp tissue between said tissue grasping surfaces, and a fastener feed member disposed in said housing for conveying a clip along said track so as to secure said fastener to said tissue.

24. The apparatus according to claim 23, wherein said jaw closing assembly is adapted to close said jaws until said tissue is grasped by said jaws and then to absorb further closing movement whereby spacing of said jaw members in a closed position depends upon thickness of said tissue, and wherein said fastener feed member is adapted to conform to said spacing of said jaw members in said closed position.

25. A tissue grasping and clipping/stapling device, comprising:
a grasping jaw assembly for grasping tissue; and
a fastener delivery and forming assembly adapted for delivering and applying a fastener to tissue grasped with said jaw assembly, and comprising a fastener pusher slidably disposed relative to said jaw assembly for pushing said fastener along a fastener conveying track toward first and second tissue grasping surfaces of said jaw assembly, wherein said fastener pusher is positionable between a wide width corresponding to said track at a maximum track spacing, and a narrow width which is smaller than said wide width, wherein said fastener pusher has two spaced distally extending members which are flexibly mounted relative to each other so as to be movable between said wide width and said narrow width.

26. A tissue grasping and clipping/stapling device, comprising:
- a grasping jaw assembly for grasping tissue; and
- a fastener delivery and forming assembly adapted for delivering and applying a fastener to tissue grasped with said jaw assembly, further comprising a push member for closing said jaw assembly so as to grasp tissue therein, wherein said push member is movable between a closing position wherein said jaw assembly is closed and an open position wherein said jaw assembly is open, and further comprising an actuator member for moving said push member, and a compressible member positioned between said push member and said actuator member whereby after said jaw assembly has gripped tissue, further movement of said actuator member is absorbed by said compressible member.

* * * * *